(12) United States Patent
Wasserman (10) Patent No.: US 11,878,163 B2
(45) Date of Patent: Jan. 23, 2024

(54) ARRAYS FOR DELIVERING TUMOR TREATING FIELDS (TTFIELDS) WITH INDIVIDUALLY ACCESSIBLE ELECTRODE ELEMENTS AND TEMPERATURE SENSORS

(71) Applicant: Novocure GmbH, Root (CH)

(72) Inventor: Yoram Wasserman, Haifa (IL)

(73) Assignee: Novocure GmbH, Root (CH)

( * ) Notice: Subject to any disclaimer, the term of this patent is extended or adjusted under 35 U.S.C. 154(b) by 447 days.

(21) Appl. No.: 17/129,088

(22) Filed: Dec. 21, 2020

(65) Prior Publication Data

US 2021/0196348 A1 Jul. 1, 2021

Related U.S. Application Data

(60) Provisional application No. 62/955,664, filed on Dec. 31, 2019.

(51) Int. Cl.
  *A61N 1/00* (2006.01)
  *A61N 1/36* (2006.01)
  *A61N 1/04* (2006.01)

(52) U.S. Cl.
  CPC ....... *A61N 1/36002* (2017.08); *A61N 1/0476* (2013.01); *A61N 1/3603* (2017.08)

(58) Field of Classification Search
  None
  See application file for complete search history.

(56) References Cited

U.S. PATENT DOCUMENTS

| | | | |
|---|---|---|---|
| 4,676,258 A | 6/1987 | Inokuchi et al. | |
| 5,081,988 A | 1/1992 | Cook et al. | |
| 6,023,638 A | * 2/2000 | Swanson | A61B 5/6855 606/41 |
| 6,868,289 B2 | 3/2005 | Palti | |
| 7,016,725 B2 | 3/2006 | Palti | |
| 7,089,054 B2 | 8/2006 | Palti | |
| 7,136,699 B2 | 11/2006 | Palti | |
| 7,146,210 B2 | 12/2006 | Palti | |
| 7,333,852 B2 | 2/2008 | Palti | |

(Continued)

FOREIGN PATENT DOCUMENTS

JP 2005117093 * 10/2003 ............... H03B 5/32

OTHER PUBLICATIONS

International Search Report and Written Opinion issued in application No. PCT/IB2020/062309 dated Mar. 23, 2021.

*Primary Examiner* — John R Downey
*Assistant Examiner* — Anant A Gupta
(74) *Attorney, Agent, or Firm* — Potomac Law Group, PLLC (57) ABSTRACT

Tumor treating fields (TTFields) can be delivered to a subject's body at higher field strengths by switching off one or more electrode elements in a transducer array that are overheating. This may be accomplished by using thermistors that sense the temperature of each electrode element. Portions of the wiring of each transducer array is shared between the electrode elements and the thermistors by using a plurality of conductors, each of which electrically connects (a) a pin of a connector, (b) a respective electrode element, and (c) a respective thermistor. In some embodiments, all of the thermistors are wired in series. In other embodiments, all the thermistors share a common connection.

9 Claims, 7 Drawing Sheets

(56) References Cited

U.S. PATENT DOCUMENTS

| | | |
|---|---|---|
| 7,467,011 B2 | 12/2008 | Palti |
| 7,519,420 B2 | 4/2009 | Palti |
| 7,565,205 B2 | 7/2009 | Palti |
| 7,565,208 B2 | 7/2009 | Palti |
| 7,599,745 B2 | 10/2009 | Palti |
| 7,599,746 B2 | 10/2009 | Palti |
| 7,706,890 B2 | 4/2010 | Palti |
| 7,715,921 B2 | 5/2010 | Palti |
| 7,805,201 B2 | 9/2010 | Palti |
| 7,890,183 B2 | 2/2011 | Palti et al. |
| 7,912,540 B2 | 3/2011 | Palti |
| 7,917,227 B2 | 3/2011 | Palti |
| 8,019,414 B2 | 9/2011 | Palti |
| 8,027,738 B2 | 9/2011 | Palti |
| 8,170,684 B2 | 5/2012 | Palti |
| 8,175,698 B2 | 5/2012 | Palti et al. |
| 8,229,555 B2 | 7/2012 | Palti |
| RE43,618 E | 8/2012 | Palti |
| 8,244,345 B2 | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,706,261 B2 | 4/2014 | Palti |
| 8,715,203 B2 | 5/2014 | Palti |
| 8,718,756 B2 | 5/2014 | Palti |
| 8,764,675 B2 | 7/2014 | Palti |
| 9,023,090 B2 | 5/2015 | Palti |
| 9,023,091 B2 | 5/2015 | Palti |
| 9,039,674 B2 | 5/2015 | Palti et al. |
| 9,056,203 B2 | 6/2015 | Palti et al. |
| 9,440,068 B2 | 9/2016 | Palti et al. |
| 9,655,669 B2 | 5/2017 | Palti et al. |
| 9,750,934 B2 | 9/2017 | Palti et al. |
| 9,910,453 B2 | 3/2018 | Wasserman et al. |
| 10,188,851 B2 | 1/2019 | Wenger et al. |
| 10,441,776 B2 | 10/2019 | Kirson et al. |
| 10,779,875 B2 | 9/2020 | Palti et al. |
| 10,821,283 B2 | 11/2020 | Giladi et al. |
| 10,953,209 B2 | 3/2021 | Story et al. |
| 2006/0167499 A1 | 7/2006 | Palti |
| 2006/0282122 A1 | 12/2006 | Palti |
| 2007/0033660 A1 | 2/2007 | Palti |
| 2007/0225766 A1 | 9/2007 | Palti |
| 2007/0239213 A1 | 10/2007 | Palti |
| 2009/0076366 A1 | 3/2009 | Palti |
| 2011/0137229 A1 | 6/2011 | Palti et al. |
| 2012/0283726 A1 | 11/2012 | Palti |
| 2013/0178819 A1 | 7/2013 | Palti et al. |
| 2013/0178820 A1 | 7/2013 | Palti et al. |
| 2013/0184637 A1 | 7/2013 | Palti |
| 2013/0184674 A1 | 7/2013 | Palti |
| 2014/0330268 A1 | 11/2014 | Palti et al. |
| 2015/0112328 A1* | 4/2015 | Willard ............ A61B 18/1492 606/41 |
| 2017/0120041 A1 | 5/2017 | Wenger et al. |
| 2017/0215939 A1 | 8/2017 | Palti et al. |
| 2017/0281934 A1 | 10/2017 | Giladi et al. |
| 2018/0001075 A1 | 1/2018 | Kirson et al. |
| 2018/0008708 A1 | 1/2018 | Giladi et al. |
| 2018/0050200 A1* | 2/2018 | Wasserman ............ A61N 1/40 |
| 2018/0160933 A1 | 6/2018 | Urman et al. |
| 2018/0202991 A1 | 7/2018 | Giladi et al. |
| 2019/0117956 A1 | 4/2019 | Wenger et al. |
| 2019/0117963 A1 | 4/2019 | Travers et al. |
| 2019/0307781 A1 | 10/2019 | Krex et al. |
| 2019/0308016 A1 | 10/2019 | Wenger et al. |
| 2020/0001069 A1 | 1/2020 | Kirson et al. |
| 2020/0009376 A1 | 1/2020 | Chang et al. |
| 2020/0009377 A1 | 1/2020 | Chang et al. |
| 2020/0016067 A1 | 1/2020 | Gotlib et al. |
| 2020/0016399 A1 | 1/2020 | Kaynan et al. |
| 2020/0023179 A1 | 1/2020 | Bomzon et al. |
| 2020/0061360 A1 | 2/2020 | Hagemann et al. |
| 2020/0061361 A1 | 2/2020 | Hagemann et al. |
| 2020/0069937 A1 | 3/2020 | Naveh et al. |
| 2020/0078582 A1 | 3/2020 | Alon et al. |
| 2020/0108031 A1 | 4/2020 | Borst et al. |
| 2020/0114141 A1 | 4/2020 | Bomzon et al. |
| 2020/0114142 A1 | 4/2020 | Bomzon et al. |
| 2020/0121728 A1 | 4/2020 | Wardak et al. |
| 2020/0129761 A1 | 4/2020 | Bomzon et al. |
| 2020/0146586 A1 | 5/2020 | Naveh et al. |
| 2020/0155835 A1 | 5/2020 | Wasserman et al. |
| 2020/0155836 A1* | 5/2020 | Chen .................. A61N 1/3718 |
| 2020/0171297 A1 | 6/2020 | Kirson et al. |
| 2020/0179512 A1 | 6/2020 | Giladi et al. |
| 2020/0219261 A1 | 7/2020 | Shamir et al. |
| 2020/0254242 A1 | 8/2020 | Chang et al. |
| 2020/0269037 A1 | 8/2020 | Hagemann et al. |
| 2020/0269041 A1 | 8/2020 | Zeevi et al. |
| 2020/0269042 A1 | 8/2020 | Giladi et al. |
| 2020/0269043 A1 | 8/2020 | Wasserman et al. |
| 2020/0306531 A1 | 10/2020 | Tran et al. |
| 2020/0330755 A1 | 10/2020 | Wasserman et al. |
| 2020/0368525 A1 | 11/2020 | Maag et al. |
| 2021/0000528 A1 | 1/2021 | Palti et al. |
| 2021/0008367 A1 | 1/2021 | Giladi et al. |
| 2021/0031031 A1 | 2/2021 | Wasserman et al. |
| 2021/0038584 A1 | 2/2021 | Voloshin-Sela |
| 2021/0060334 A1 | 3/2021 | Avraham et al. |
| 2021/0069503 A1 | 3/2021 | Tran et al. |

* cited by examiner

PRIOR ART

ARRAYS FOR DELIVERING TUMOR TREATING FIELDS (TTFIELDS) WITH INDIVIDUALLY ACCESSIBLE ELECTRODE ELEMENTS AND TEMPERATURE SENSORS

CROSS REFERENCE TO RELATED APPLICATIONS

This application claims the benefit of U.S. Provisional Application 62/955,664, filed Dec. 31, 2019, which is incorporated herein by reference in its entirety.

BACKGROUND

Figure 1:
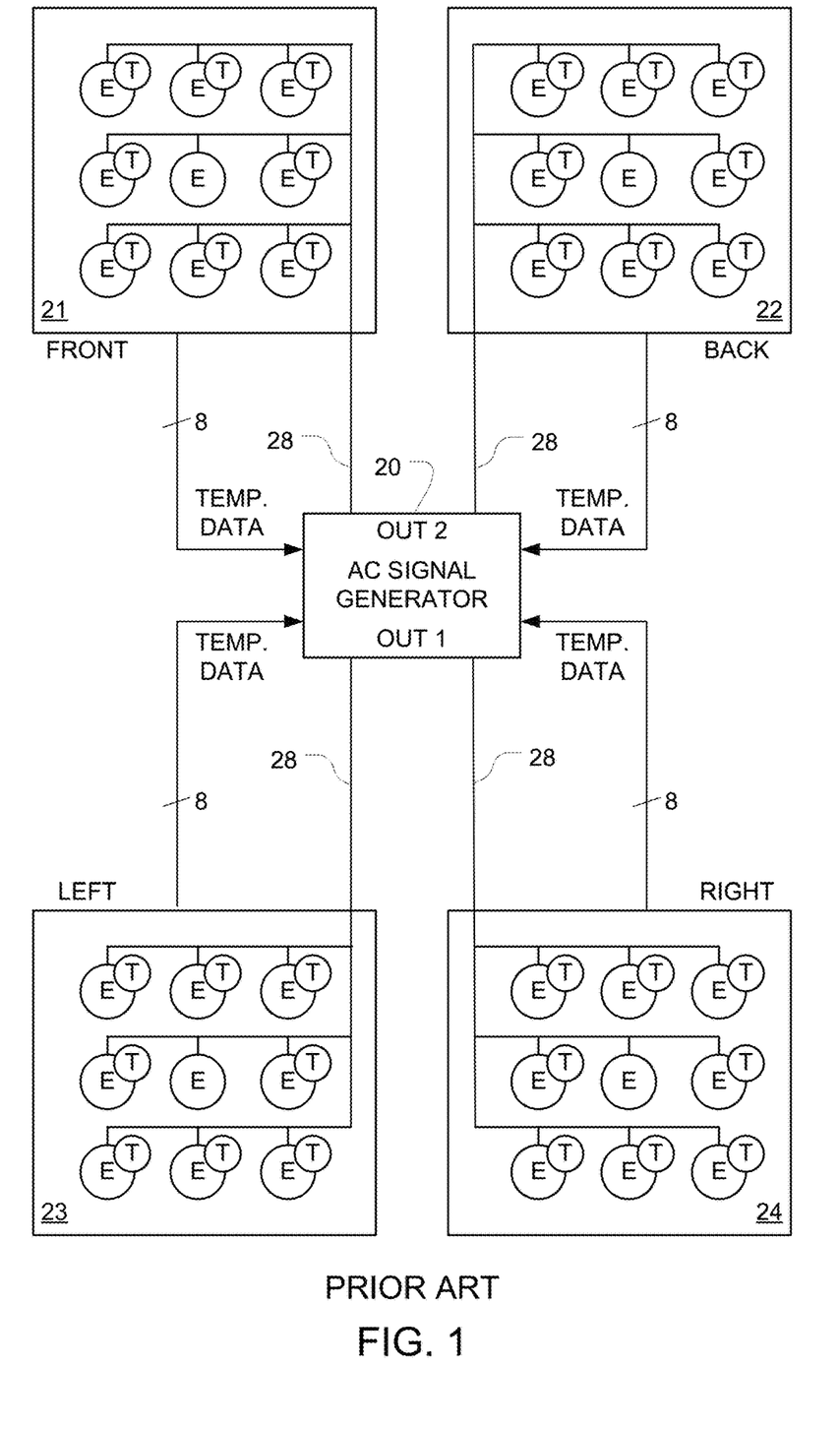
FIG. 1 is a schematic representation of the prior art Optune® system for delivering TTFields.
Figure 2A:
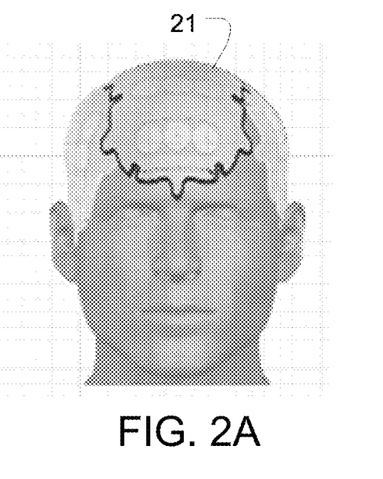
FIGS. 2A-2D depict the positioning of transducer arrays on a person's head for treating a brain tumor.
Figure 2B:
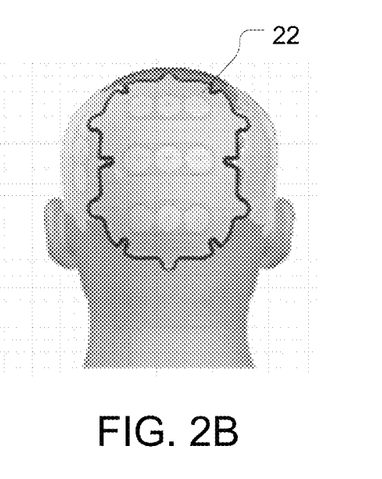
Figure 2C:
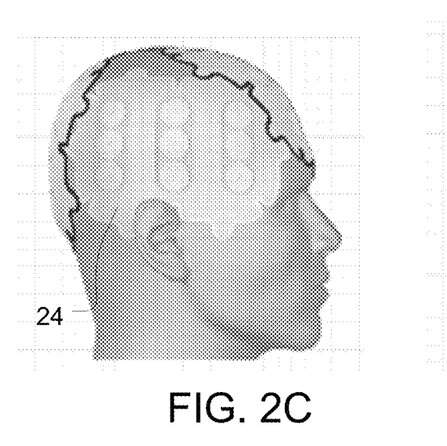
Figure 2D:
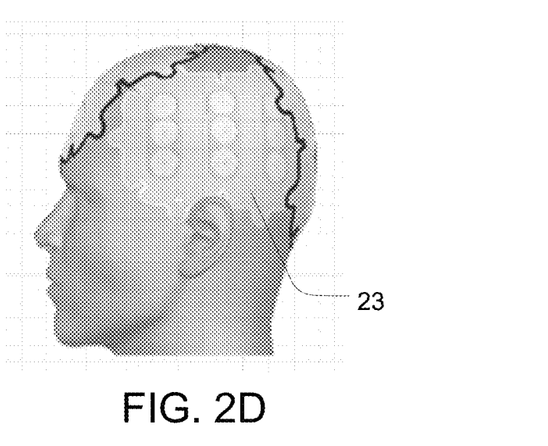

TTFields therapy is a proven approach for treating tumors. FIG. 1 is a schematic representation of the prior art Optune® system for delivering TTFields. The TTFields are delivered to patients via four transducer arrays 21-24 that are placed on the patient's skin in close proximity to a tumor (e.g., as depicted in FIGS. 2A-2D for a person with glioblastoma). The transducer arrays 21-24 are arranged in two pairs, and each transducer array is connected via a multi-wire cable to an AC signal generator 20. The AC signal generator (a) sends an AC current through one pair of arrays 21, 22 during a first period of time, which induces an electric field with a first direction through the tumor; then (b) sends an AC current through the other pair of arrays 23, 24 during a second period of time, which induces an electric field with a second direction through the tumor; then repeats steps (a) and (b) for the duration of the treatment.

Each transducer array 21-24 is configured as a set of capacitively coupled electrode elements E (e.g., a set of 9 electrode elements, each of which is about 2 cm in diameter) that are interconnected via a flex circuit. Each electrode element includes an electrically conductive substrate with a dielectric layer (more specifically, a layer of ceramic material with a high dielectric constant) disposed thereon. Each electrode element is sandwiched between a layer of an electrically conductive medical gel and an adhesive tape. When placing the arrays on the patient, the medical gel conforms to the contours of the patient's skin and ensures good electric contact of the device with the body. The adhesive tape holds the entire array in place on the patient as the patient goes about their daily activities.

The amplitude of the alternating current that is delivered via the transducer arrays is controlled so that skin temperature (as measured on the skin below the transducer arrays) does not exceed a safety threshold of 41° C. The temperature measurements on the patient's skin are obtained using thermistors T placed beneath some of the disks of the transducer arrays. In the existing Optune® system, each array includes 8 thermistors, with one thermistor positioned beneath a respective disk in the array. (Note that most arrays include more than 8 disks, in which case the temperature measurements are only performed beneath a sub-set of the disks within the array).

The AC signal generator 20 obtains temperature measurements from all 32 thermistors (4 arrays×8 thermistors per array), and the controller in the AC signal generator uses the temperature measurements to control the current to be delivered via each pair of arrays in order to maintain temperatures below 41° C. on the patient's skin. The current itself is delivered to each array via an additional wire (i.e., one wire 28 for each of the arrays 21-24) that runs from the AC signal generator 20 to each array. And an additional wire (not shown) for each of the arrays 21-24 is used as a common return for all 8 thermistors. Thus, each of the four cables that terminate on the arrays 21-24 in the existing Optune system has a total of 10 conductors.

SUMMARY OF THE INVENTION

One aspect of the invention is directed to a first apparatus for applying an alternating electric field to a subject's body. The first apparatus comprises a plurality of electrode elements; a support configured to hold the electrode elements against the subject's body; and a plurality of thermistors. Each of the thermistors has a first terminal and a second terminal, and each of the thermistors is positioned to sense a temperature at a corresponding respective one of the electrode elements. The first apparatus also comprises a connector having a plurality of first pins and a second pin; a plurality of first conductors, each of which provides an electrically conductive path between (a) a respective one of the first pins, (b) a respective one of the electrode elements, and (c) the first terminal of the corresponding thermistor; and a second conductor that provides an electrically conductive path between the second pin and the second terminal of at least one of the thermistors.

In some embodiments of the first apparatus, the second terminals of all the thermistors are wired together. Optionally, in these embodiments, the second terminals of all the thermistors may be wired together using at least one of (a) at least one trace on a flex circuit and (b) at least one wire.

In some embodiments of the first apparatus, the plurality of thermistors are arranged in series, beginning with a first one of the thermistors and ending with a last one of the thermistors, and the second terminal of each of the thermistors except for the last thermistor is wired to the first terminal of a respective subsequent thermistor, and the second conductor provides an electrically conductive path between the second pin of the connector and the second terminal of the last thermistor.

In some embodiments of the first apparatus, the second conductor provides an electrically conductive path between the second pin and the second terminal of only a single one of the thermistors.

In some embodiments of the first apparatus, the plurality of electrode elements comprises at least four electrode elements, and the plurality of thermistors comprises at least four thermistors.

In some embodiments of the first apparatus, the plurality of electrode elements comprises at least nine electrode elements, and the plurality of thermistors comprises at least nine thermistors.

In some embodiments of the first apparatus, each of the electrode elements comprises a conductive plate and a dielectric layer disposed on the conductive plate, and the support is configured to hold the electrode elements against the subject's body so that the dielectric layer of each of the electrode elements faces the subject's body.

In some embodiments of the first apparatus, the second terminals of all the thermistors are wired together, and the second conductor provides an electrically conductive path between the second pin and the second terminal of all the thermistors.

Another aspect of the invention is directed to a second apparatus for applying an alternating electric field to a subject's body using a plurality of electrode elements. Each of the plurality of electrode elements is disposed in thermal contact with a respective thermistor. The second apparatus comprises an AC signal generator that generates an AC output signal, and a connector that includes a plurality of pins. Each of the pins corresponds to a respective one of the plurality of electrode elements. The second apparatus also comprises a first plurality of switches. Each of the first plurality of switches is configured to selectively either apply or not apply the AC output signal to a respective one of the pins. The second apparatus also comprises an amplifier configured to accept an electrical signal from each of the thermistors and generate a corresponding output. The electrical signals from the thermistors arrive via the same pins that correspond to the plurality of electrode elements. The second apparatus also comprises a controller configured to, based on the output of the amplifier, control the first plurality of switches so as to individually adjust the duty cycle of the AC signal that is applied to each of the plurality of pins.

In some embodiments of the second apparatus, the controller is configured to (a) determine, based on the output of the amplifier, when at least one of the electrode elements is hotter than other electrode elements and (b) control the first plurality of switches so as to reduce the duty cycle of the AC signal that is applied to at least one respective pin. In some embodiments of the second apparatus, the controller is configured to (a) determine, based on the output of the amplifier, when at least one of the electrode elements is hotter than a threshold level and (b) control the first plurality of switches so as to reduce the duty cycle of the AC signal that is applied to at least one respective pin.

In some embodiments of the second apparatus, the plurality of electrode elements comprises at least four electrode elements, the plurality of pins comprises at least four pins, and the first plurality of switches comprises at least four switches. In some embodiments of the second apparatus, the plurality of electrode elements comprises at least nine electrode elements, the plurality of pins comprises at least nine pins, and the first plurality of switches comprises at least nine switches.

Some embodiments of the second apparatus further comprise a second plurality of switches, each of which is arranged to route a signal from a respective one of the plurality of pins to a first input of the amplifier. In these embodiments, the controller is further configured to control the second plurality of switches so as to sequentially select each of the plurality of pins and to sequentially obtain temperature readings from each of the thermistors. Optionally, in these embodiments, the connector includes an additional pin, and the apparatus further comprises an additional switch arranged to route a signal from the additional pin to a second input of the amplifier.

Some embodiments of the second apparatus further comprise a second plurality of switches, each of which is arranged to route a signal from a respective one of the plurality of pins to a first input of the amplifier. In these embodiments, the controller is further configured to control the second plurality of switches so as to sequentially select each of the plurality of pins and to sequentially obtain temperature readings from each of the thermistors. The connector includes an additional pin, and the apparatus further comprises (a) an additional switch arranged to route a signal from the additional pin to a second input of the amplifier; and (b) a third plurality of switches, each of which is arranged to route a signal from a respective one of the plurality of pins to the additional pin. In these embodiments, the controller is further configured so that when a given switch from the first plurality of switches is opened, the controller closes a respective corresponding switch from the third plurality of switches.

Some embodiments of the second apparatus further comprise a second plurality of switches, each of which is arranged to route a signal from a respective one of the plurality of pins to a first input of the amplifier; and a third plurality of switches, each of which is arranged to route a signal from a respective one of the plurality of pins to a second input of the amplifier. In these embodiments, the controller is further configured to control the second plurality of switches and the third plurality of switches so as to sequentially route signals to the first and second inputs of the amplifier from pairs of the plurality of pins that correspond to both terminals of each of the thermistors in turn, and to sequentially obtain temperature readings from each of the thermistors.

Another aspect of the invention is directed to a first method of applying an alternating electric field to a subject's body using a plurality of electrode elements. Each of the plurality of electrode elements is disposed in thermal contact with a respective thermistor. The first method comprises applying an AC signal to each of the electrode elements at a respective duty cycle so that an alternating electric field is induced within the subject; inputting a signal from each of the thermistors; determining, based on the inputted signals, a temperature of each of the electrode elements; and adjusting the duty cycle of the AC signals that are applied to the electrode elements based on the determined temperatures. After the adjusting, the duty cycle of the AC signal that is applied to at least one of the electrode elements differs from the duty cycle of the AC signal that is applied to another one of the electrode elements.

In some instances of the first method, the adjusting comprises reducing the duty cycle of the AC signal that is applied to at least one of the electrode elements that is hotter than at least one other electrode element. In some instances of the first method, the adjusting comprises reducing the duty cycle of the AC signal that is applied to whichever one of the electrode elements is hottest. In some instances of the first method, the adjusting comprises reducing the duty cycle of the AC signal that is applied to any of the electrode elements whose temperature exceeds a threshold level.

In some instances of the first method, the adjusting comprises reducing the duty cycle of the AC signal that is applied to any of the electrode elements whose rate of heating exceeds a threshold level. In some instances of the first method, the adjusting comprises switching off the AC signals that are applied to any of the electrode elements whose temperature exceeds a first threshold level, and switching on the AC signals that are applied to at least one of the electrode elements whose temperature is below a second threshold level, where the second threshold level is lower than the first threshold level.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

Although the FIG. 1 approach described above is very effective for delivering TTFields to a tumor, the effectiveness of the treatment will drop if good electrical contact is not maintained between each of the elements in the four transducer arrays 21-24 and the person's body. This can happen, for example, if the hydrogel beneath one or more elements of the transducer arrays dries out over time, or due to hair growth beneath one or more of the elements.

Assume, for example, that there are 9 electrode elements E in each of the transducer arrays 21-24, that the hydrogel beneath a single electrode element E on the front transducer array 21 has dried out; and that enough hydrogel is present beneath (a) all the other electrode elements E of that transducer array 21, and (b) all the electrode elements E of the other transducer arrays 22-24. In this situation, the resistance between the single electrode element E and the person's body will be higher than the resistance between any of the other electrode elements and the person's body. And this increase in resistance will cause the temperature of the single electrode element E to rise more than the other electrode elements.

In this situation, because all of the electrode elements E in each of the transducer arrays 21-24 are wired in parallel, the AC signal generator 20 must limit the current that is applied to the entire front/back pair of transducer arrays 21, 22 in order to keep the temperature of the single electrode element E on the front array 21 below 41°, even though the temperature at all the remaining electrode elements E on the front and back transducer arrays 21, 22 may be well below 41° C. And this decrease in current causes a corresponding decrease in the strength of the electric field at the tumor, which can reduce the efficacy of the treatment.

The embodiments described herein advantageously provide the ability to control the current that is routed through individual electrode elements, without unduly increasing the number of conductors in the cables that terminate on the transducer arrays, and without relying on active components positioned on or near the transducer arrays.

Unlike the prior art configuration, in which all of the electrode elements E in each of the transducer arrays 21-24 are wired in parallel, the embodiments described herein have an individual conductor for each of the plurality of electrode elements in each of the transducer arrays. This configuration makes it possible to independently switch the current on and off for any given individual electrode element in any one of the arrays.

One possible approach for controlling the current on an element-by-element basis is to start off with the prior art configuration depicted in FIG. 1, rewire the electrode elements so that they are not connected in parallel, and run an individual wire to each individual electrode element. A problem with this approach, however, is that it requires almost double the number of conductors in each of the cables that runs to the transducer arrays. For example, in transducer arrays that have 9 electrode elements, a total of 19 wires would be needed in each cable (i.e., 9 to provide individual access to each of the 9 electrode elements, an additional 9 for the signals from the thermistors, plus one additional wire to serve as a common return for all 9 thermistors). And this dramatic increase in the number of wires in each cable tends to make the cables less flexible and more cumbersome, which can make the system harder to use, and reduce patient compliance.

One way to reduce the total number of wires in each cable is to position active components (e.g., electronically controlled switches) on or near the transducer arrays. For example, a set of switches may be used to control which of the electrode elements is turned on at any given moment (e.g., as described in U.S. Ser. No. 16/686,918, filed Nov. 18, 2019, which is incorporated herein by reference in its entirety). Alternatively or additionally, an analog multiplexer may be used to multiplex the temperature readings obtained from the thermistors into a cable that has a small number of conductors (e.g., as described in US 2018/0050200, which is incorporated herein by reference in its entirety). But positioning active components on or near the transducer arrays introduces its own set of drawbacks (e.g., added weight and complexity, plus potential issues with sterilization).

Figure 3:
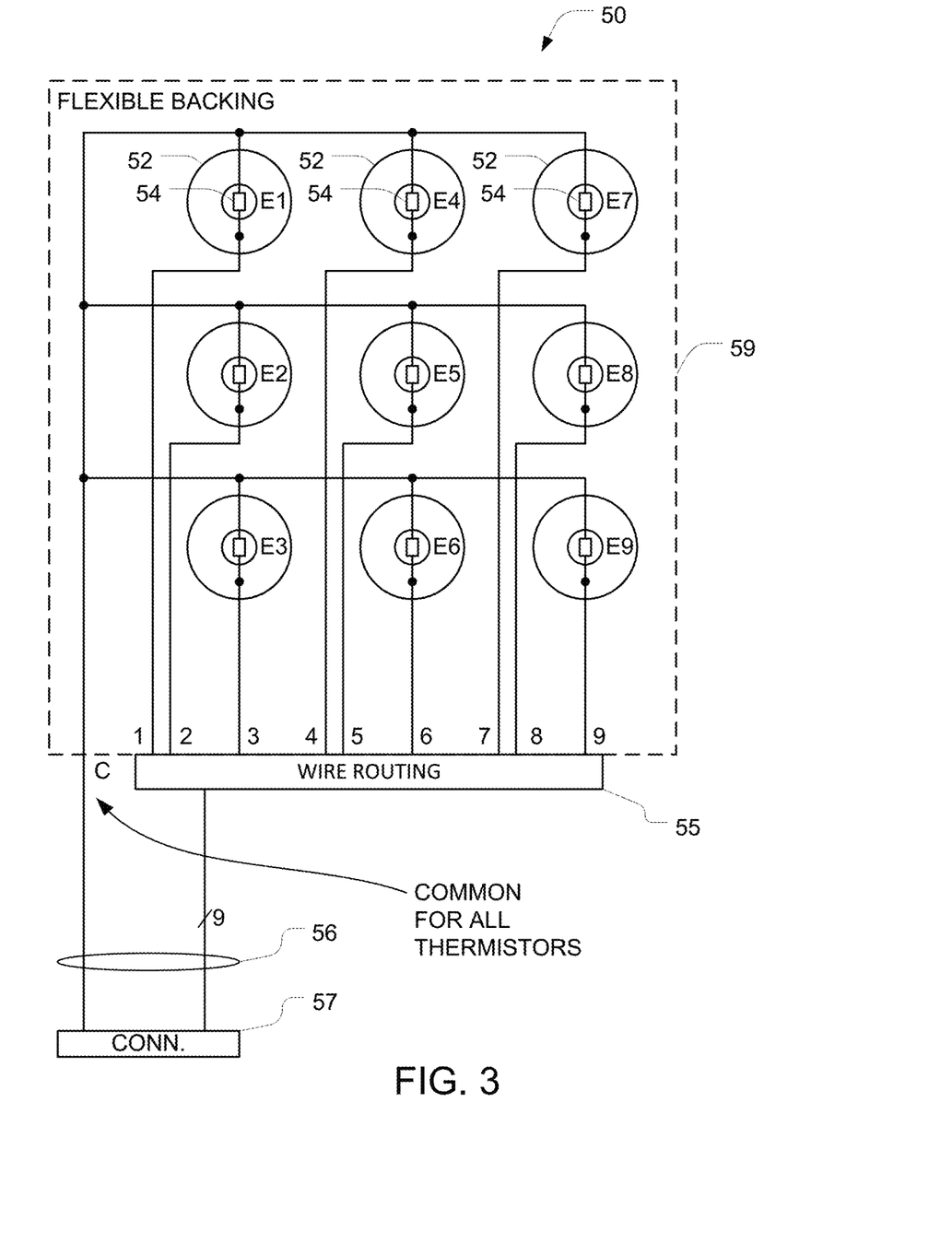
FIG. 3 depicts a first embodiment of a transducer array that provides an individual conductor for each individual electrode element.

FIG. 3 depicts a first embodiment of a transducer array 50 that provides an individual conductor for each individual electrode element 51 without causing a dramatic increase in the number of wires in each cable that runs to a given transducer array, and without requiring active components positioned on or near the transducer arrays. As will be described below in connection with FIG. 4, four copies of the transducer array 50 are preferably used to administer TTFields treatment to a person's head (or other body part).

Each transducer array 50 includes a plurality of electrode elements 52, which are labeled E1-E9 for ease of reference in the FIG. 3 embodiment. Each of these electrode elements 52 has an electrically conductive substrate (e.g., a round metal substrate) with a dielectric layer disposed thereon. In some preferred embodiments, each of these electrode elements 52 is a disc-shaped capacitively coupled electrode element (e.g., with a 2 cm diameter) that is similar to the prior art electrode elements used in the Optune® system, and the dielectric layer comprises a thin layer of ceramic material with a high dielectric constant. However, unlike the Optune® system and FIG. 1 (in which all the elements are wired in parallel), an individual conductor runs from each of the electrode elements 52 to the connector 57 in this FIG. 3 embodiment. These conductors are numbered 1-9 just above the "wire routing" block 55 (which funnels the individual conductors together into a single cable 56). In some preferred embodiments, the electrical connection to each of the electrode elements 52 comprises one or more traces on a flex circuit and/or one or more conductive wires.

In the embodiment depicted in FIG. 3, all of the capacitively coupled electrode elements 52 are held in place by a support structure 59. The support structure is configured to hold the electrode elements against the subject's body so that the dielectric layer of the electrode elements 52 faces the subject's body and can be positioned in contact with the subject's body. Optionally, this support structure may comprise a flexible backing 59 (e.g., a layer of foam material). Preferably, a layer of hydrogel is disposed between the dielectric layer of the electrode elements 52 and the subject's body when the transducer array 50 is placed against the subject's body. Construction of the support structure 59 may be implemented using any of a variety of conventional approaches that will be apparent to persons skilled in the relevant arts, including but not limited to self-adhesive fabric, foam, or plastic sheeting.

Each transducer array 50 also includes a plurality of thermistors 54, with one thermistor positioned at each of the electrode elements 52 so that the thermistor 54 can sense the temperature of a respective electrode element 52. This may be accomplished, for example, by incorporating a hole or well in the center of each electrode element 52, and positioning a respective one of the thermistors 54 in this hole or well. Each of the thermistors 54 has a first terminal (i.e., the lower terminal of the thermistor in FIG. 3) and a second terminal (i.e., the upper terminal of the thermistor in FIG. 3).

Each transducer array 50 also has a connector 57 that is used to send electrical signals into and out of the transducer array 50. The connector 57 has a plurality of first pins and a second pin. In the illustrated embodiment, the number of first pins is the same as the number of electrode elements 52, and each of the first pins corresponds to a respective one of those electrode elements 52. And in the illustrated embodiment, there is only a single second pin, labeled C. Note that as used herein, the term "pin" can refer to either a male or female pin of the connector 57.

Each transducer array 50 also has a plurality of first conductors, and the number of these first conductors will depend on the number of electrode elements 52. In the embodiment depicted in FIG. 3, which contains 9 electrode elements 52, these conductors are labeled 1-9. Each of these first conductors provides an electrically conductive path between (a) a respective one of the first pins in the connector 57, (b) the conductive substrate of a respective one of the electrode elements 52 (E1-E9), and (c) the first terminal of the corresponding thermistor 54. Note that each of these first conductors may optionally be implemented using a plurality of segments of wire and/or a plurality of traces on a flex circuit.

Each transducer array 50 also has a second conductor that provides an electrically conductive path between the second pin of the connector 57 and the second terminal (i.e., the upper terminal in FIG. 3) of at least one of the thermistors 54. In the embodiment depicted in FIG. 3, the second terminal of all of the thermistors are wired together. In this embodiment, the second conductor provides an electrically conductive path between the second pin of the connector 57 and the second terminal of all of the thermistors 54. The second conductor may optionally be implemented using a plurality of segments of wire and/or a plurality of traces on a flex circuit.

Because the connector 57 has an individual first pin that corresponds to each of the individual electrode elements 52, and because an electrically conductive path exists between each of the first pins and a respective one of the electrode elements 52, the system that mates with the connector 57 can selectively energize or not energize each of the electrode elements 52 individually by either applying or not applying a signal to the respective first pin on the connector 57.

And because the connector 57 has an individual first pin that corresponds to the first terminal of each of the thermistors 54 and because an electrically conductive path exists between each of the first pins and a respective one of the thermistors 54, the system that mates with the connector 57 has access to the first terminal of each of the thermistors 54. In addition, because the second terminal of all the thermistors 54 are all wired together and connected to the second pin (labeled C), the system that mates with the connector 57 also has access to the second terminal of each of the thermistors 54. As a result, the system that mates with the connector 57 can measure the resistance of any of the thermistors 54. This may be accomplished, for example, by routing a known current through each thermistor 54 and measuring the voltage that appears across each thermistor.

Notably, because any given first pin on the connector 57 corresponds to a respective one of the individual electrode elements 52 and also corresponds to a respective one of the individual thermistors 54, each of the first pins on the connector 57 serves two functions. This reduces the number of wires that must be included in each of the cables 56, which in turn advantageously makes the cables more flexible and less cumbersome.

Figure 4:
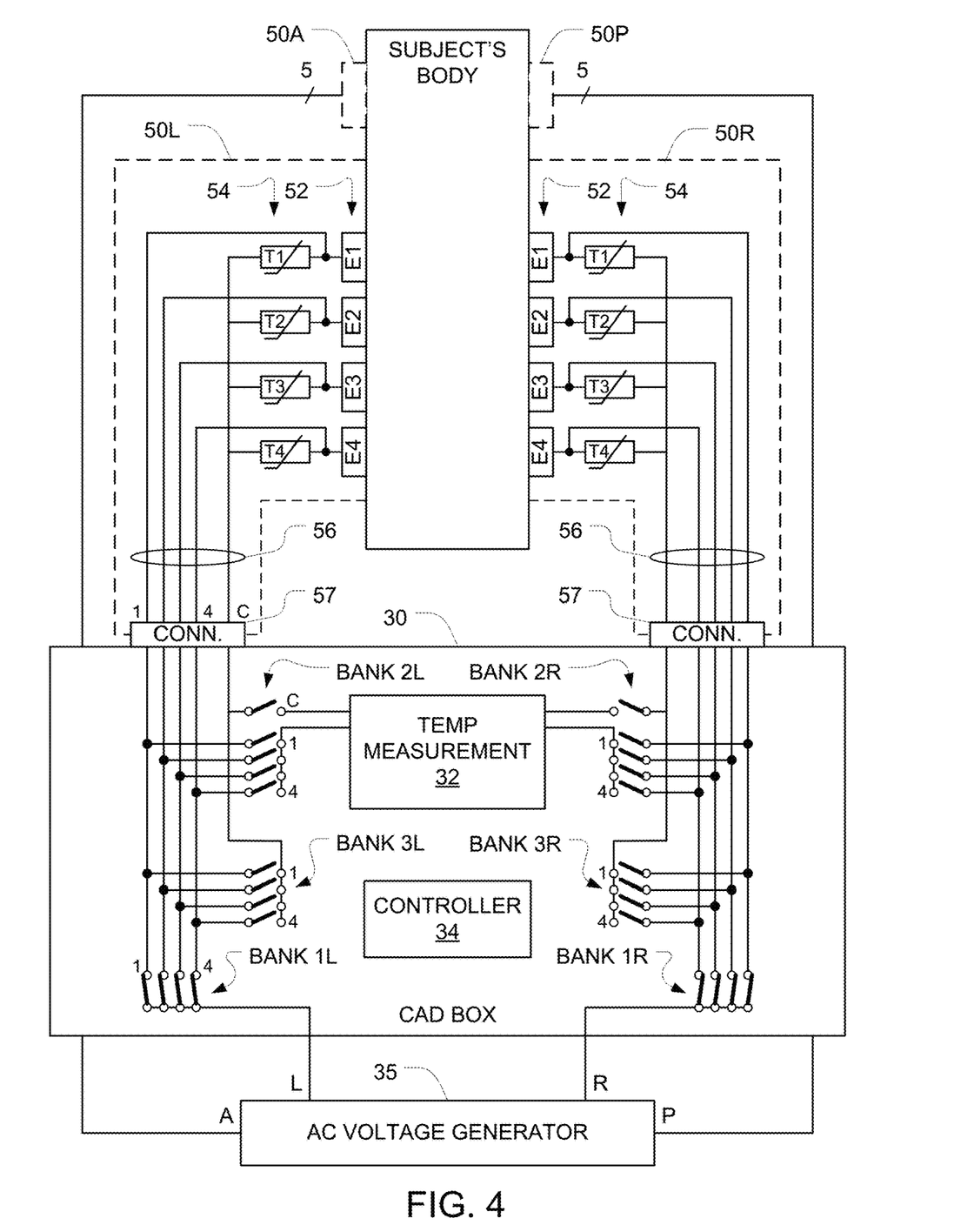
FIG. 4 is a block diagram of a system that uses four copies of the FIG. 3 transducer array to apply TTFields to a subject.

FIG. 4 is a block diagram of a system that uses four copies of the transducer array 50 (described above in connection with FIG. 3) to apply TTFields to a subject. In FIG. 4, these four copies are labeled 50A, 50P, 50L, and 50R, where A, P, L, and R stand for anterior, posterior, left, and right, respectively. The lower portion of FIG. 4 depicts an AC voltage generator 35 and a "CAD box" 30 as separate blocks, the latter of which includes a temperature measurement block 32, a controller 34, and banks of switches 1L, 2L, 3L, 1R, 2R, and 3R. In some embodiments, the components in those two blocks 35, 30 may be physically divided into two separate housings. But in alternative embodiments, the components in those two blocks 35, 30 are combined into a single housing.

For clarity, only the left and right channels are depicted in FIG. 4. But the remaining channels (i.e., the anterior and posterior channels) operate in the same way as the left and right channels, respectively. Additionally, each of the transducer arrays 50 in FIG. 4 is depicted with only 4 electrode elements 52 and four thermistors 54 for clarity. But it is expected that practical systems will have a larger number (e.g., between 9 and 30) of electrode elements and thermistors, and will also have a larger number of certain other components (e.g., switches, conductors, etc.), depending on the number of electrode elements 52 that are actually used in each of the transducer arrays 50.

The FIG. 4 system can measure the temperatures of the thermistors 54 in the left channel 50L by controlling the electronically-controlled switches in bank 2L (which may be implemented using bidirectional analog switches) to select each of the thermistors in turn. For example, switch C and switch 1 should be closed to select thermistor T1; switch C and switch 2 should be closed to select thermistor T2; etc. After any given one of the thermistors T1-T4 within the transducer array 50L has been selected, the temperature measurement block (TMB) 32 can determine the temperature of the thermistor by measuring the resistance of the thermistor. This may be accomplished, for example, by using a current source that generates a known current (e.g., 150 µA) positioned within the TMB 32, so that the known current will be routed into whichever thermistor is selected by the bank of switches 2L at any given instant. The known current will cause a voltage to appear across the selected thermistor (T1-T4), and the temperature of the selected thermistor can be determined by measuring this voltage. A controller 34 runs a program that selects each of the thermistors T1-T4 in turn and measures the voltage that appears across each of the thermistors (which is indicative of the temperature at the selected thermistor) in turn. An example of suitable hardware and procedures that may be used to obtain temperature readings from each of the thermistors is described in US 2018/0050200, which is incorporated herein by reference in its entirety.

Measuring the temperature of the thermistors 54 in the right channel 50R is accomplished using the same approach described above in connection with the left channel 50L, except that the bank of switches 2R is used instead of bank 2L. Corresponding banks of switches (not shown) are also provided for the other channels 50A, 50P, and a similar approach is used in those channels as well.

Based on the temperature readings obtained from the thermistors 54 (T1-T4), the controller 34 controls the switches in bank 1L to either turn on or turn off the current (which originates in the AC voltage generator 35) to each of the corresponding electrode elements 52 (E1-E4). For example, to leave the current on for all four of the electrode elements 52, all four of the switches in bank 1L should be closed. To interrupt the current that reaches electrode element E1, switch 1 in bank 1L should be opened; and to interrupt the current that reaches electrode element E2, switch 2 in bank 1L should be opened; etc.

Controlling the current that is routed through individual electrode elements can be used to reduce or eliminate the decrease in average current that is coupled into the person's body when a small number of electrode elements begins to overheat. This, in turn, can advantageously reduce or eliminate the decrease in strength of the electric field at the tumor. This may be accomplished by programming the controller 34 to alternately switch the current on and off for each individual electrode element that begins to approach 41° in order to reduce the average current for those electrode elements, without affecting the current that passes through the remaining electrode elements (which are not approaching 41°).

Assume, for example, a situation in which 500 mA of current is passing through a transducer array that includes 10 electrode elements, and only a single one of those electrode elements begins to approach 41°. Assume further that a 10% reduction of current through the single electrode element would be necessary to keep the temperature at that single electrode element below 41°. Instead of achieving this 10% reduction in current by cutting the current through the entire transducer array from 500 mA to 450 mA (as in the prior art), the controller 34 can cut the average current through the single electrode element by 10% by controlling the switches in bank 1L to switch the current through that single electrode element on and off with a 90% duty cycle, while leaving the current on full-time for all the remaining electrode elements. Note that the switching rate must be sufficiently fast so that the instantaneous temperature at the single electrode element never exceeds 41°, in view of the thermal inertia of the electrode elements. For example, a 90% duty cycle could be achieved by switching the current on for 90 ms and switching the current off for 10 ms.

When this approach is used, the current through the remaining 9 electrode elements can remain unchanged (i.e., 50 mA per electrode element), and only the current through the single electrode element is reduced to an average of 45 mA. The average net total current through the transducer array will then be 495 mA (i.e., 9×50+45), which means that significantly more current can be coupled into the person's body without exceeding 41° at any of the electrode elements.

The controller 34 may even be configured to increase the current through the remaining nine electrode elements in order to compensate for the reduction in current through the single electrode element. For example, the current through the remaining nine electrode elements could be increased to 50.5 mA per electrode element (e.g., by the controller 34 sending a request to the AC voltage generator 35 to increase the voltage by 1%). If this solution is implemented, the average net total current through the entire transducer array would be (9 electrodes×50.5 mA+1 electrode×50.5 mA×0.9 duty cycle)=499.95 mA, which is extremely close to the original 500 mA of current.

If, at some subsequent time (or even at the same time), the temperature at a second electrode element begins to approach 41°, a similar technique (i.e. a reduction in the duty cycle from 100% to something less than 100%) may be used to prevent the temperature at the second electrode element from exceeding 41°.

In some embodiments, this technique may be used to individually customize the duty cycle at each of the electrode elements in order to maximize the current that flows through each of those electrode elements while keeping the temperature at each of those elements below 41°. Optionally, instead of taking remedial action to reduce the duty cycle only when the temperature at a given electrode element begins to approach 41°, the controller 34 may be configured to proactively set the duty cycle at each of the electrode elements in a given transducer array individually so as to equalize the temperature across all of the electrode elements in the array. For example, the controller 34 could be configured to individually set the duty cycle at each electrode element so as to maintain a temperature that hovers around 40.5° at each of the electrode elements. Optionally, the controller 34 may be configured to send a request to the AC voltage generator 35 to increase or decrease the voltage as required in order to achieve this result.

This approach can be used to ensure that each and every electrode element will carry the maximum average current possible (without exceeding 41°), which will provide an increased field strength in the tumor and a corresponding improvement in the treatment.

In some embodiments, the controller 34 may be programmed to keep the temperature at all of the electrode elements below a safety threshold (e.g., below 41° C.) as follows: Begin by closing all of the switches 1-4 in bank 1L, so that the current is continuously on (i.e., with a 100% duty cycle). Then, based on signals arriving via the TMB 32, the controller 34 determines whether the temperature at each of the electrode elements exceeds an upper threshold (e.g., 40° C.) that is below the safety threshold. When the controller 34 detects this condition, the controller 34 reduces the duty cycle for the corresponding switch in bank 1L by toggling a corresponding digital output at the desired duty cycle. This will interrupt the current to the corresponding electrode element 52 at the same duty cycle, thereby reducing the average current at the specific electrode elements 52 whose temperature exceeds that upper threshold. The level of reduction in current is determined by the duty cycle. For example, using a 50% duty cycle will cut the current by half; and using a 75% duty cycle will cut the current by 25%.

Notably, this procedure only interrupts the current to specific ones of the electrode elements 52 on the transducer array 50, and does not interrupt the current to the remaining electrode elements 52 on that transducer array 50. This provides a very significant advantage over the prior art, because it eliminates or reduces the need to cut the current that is being routed through the electrode elements when only a small number of those electrode elements are getting hot.

A numeric example will be useful to illustrate this point. Assume, in the FIG. 4 embodiment, that the left and right transducer arrays 50L, 50R are positioned on the left and right sides of a subject's head, respectively; that all of the switches in banks 1L and 1R in the ON state with a 100% duty cycle; and that the AC voltage generator 35 is initially outputting 500 mA of current. An AC voltage will appear between the electrode elements 52 of the left transducer array 50L and the electrode elements 52 of the right transducer array 50R, and the 500 mA AC current will be capacitively coupled through the electrode elements 52 through the subject's head. The controller 34 monitors the temperature at each of the electrode elements 52 in each of the transducer arrays 50L, 50R by inputting signals from each of the temperature sensors 54 via the temperature measurement block 32. Now assume that the temperature at a given one of the electrode elements 52 in the left transducer array 50L has risen to 40° C. This condition will be reported to the controller 34 via a signal from the corresponding temperature sensor 54. When the controller 34 recognizes that the temperature of the given electrode element 52 has risen to 40° C., the controller 34 will toggle the control signal that goes to the corresponding switch in bank 1L at the desired duty cycle in order to periodically interrupt the current to the given electrode element 52 and maintain a lower average current.

This stands in sharp contrast with the prior art devices which had to decrease the current that flows through ALL of the electrode elements as soon as the temperature at even a single one of the electrode elements 52 approached 41° C.

Note that if the duty cycle at only one of the remaining electrode elements 52 is being reduced, it may be possible to maintain the original 500 mA current (and enjoy the advantages that arise from using the full current). However, if the duty cycle at a large enough number of the electrode elements 52 is being reduced, the original 500 mA current may have to be dropped. To accomplish this, the controller 34 can send and instruction to the AC voltage generator 35. When the AC voltage generator 35 receives this request, the AC voltage generator 35 will reduce its output voltage, which will cause the current to drop.

Optionally, the duty cycle that is selected by the controller 34 may be controlled based on the speed at which the given electrode element 52 heats up after current is applied to the given electrode element 52 (as measured via the temperature sensors 54 and the TMB 32). More specifically, if the controller 34 recognizes that a given electrode element 52 is heating up twice as fast as expected, the controller 34 can select a duty cycle of 50% for that electrode element. Similarly, if the controller 34 recognizes that a given electrode element 52 is heating up 10% faster than expected, the controller 34 can select a duty cycle of 90% for that electrode element.

In other embodiments, instead of deterministically cutting the average current by reducing the duty cycle, the controller 34 can reduce the average current at a given electrode element 52 based on real-time temperature measurements by using the switches in bank 1L to turn off the current to the given electrode element 52 as described above, and waiting until temperature measured using the temperature sensors 54 drops below a second temperature threshold (e.g., below 38° C.). Once the temperature drops below this second temperature threshold, the controller 34 can restore the current to the given electrode element 52. This may be accomplished, for example, by controlling the state of switch in bank 1L that was previously turned off so that it reverts to the ON state, which will allow current to flow between the electrical conductor and the respective electrode element 52. In these embodiments, the current to a given electrode element 52 may be repeatedly switched off and on based on real-time temperature measurements in order to keep the temperature at the given electrode element 52 below the safety threshold.

Individually switching the current to each of the electrode elements 52 in the right channel 50R is accomplished using the same approach described above in connection with the left channel 50L, except that the bank of switches 1R is used instead of bank 1L. Corresponding banks of switches (not shown) are also provided for the other channels 50A, 50P, and a similar approach is used in those channels as well.

Note that the examples described above (which refer to duty cycles of 100%, 90%, 75%, 50%, etc.) refer to the duty cycles within those windows of time that a given channel (e.g., the left/right channel) is active. In some preferred embodiments, the AC signal generator 35 (a) sends an AC current through the anterior/posterior arrays 50A/50P during a first period of time (e.g., 1 sec.), which induces an electric field with a first direction through the tumor in the subject's body; then (b) sends an AC current through the left/right arrays 50L/50R during a second period of time (e.g., 1 sec.), which induces an electric field with a second direction through the tumor; then repeats steps (a) and (b) for the duration of the treatment. In these embodiments, the overall duty cycle for any given channel (i.e., either the A/P channel or the L/R channel) will be half of the value in the examples described above. This is because operating at a 100% duty cycle during a 1 s window of time followed by remaining off during the next 1 s window of time results in an overall duty cycle of 50%. Similarly, operating at a 90% duty cycle during a 1 s window of time followed by remaining off during the next 1 s window of time results in an overall duty cycle of 45%.

Optionally, an additional bank of switches 3L may be provided. Each of the switches in this bank is wired in parallel with a corresponding one of the thermistors T1-T4, so that when a given one of the switches 1-4 is closed, a respective one of the thermistors T1-T4 will be shorted out.

The reason for including the additional bank of switches 3L is that when (a) current from the AC voltage generator 35 is flowing through the electrode elements 52 of the left channel 50L, the subject's body, and the electrode elements 52 of the right channel 50, and (b) the power to any of the electrode elements 52 of the left channel 50L is switched off by a corresponding one of the switches in bank 1L, current can sneak through the thermistors 54 in the left channel 50L. Assume, for example, that only switch #2 in bank 1L is switched off (i.e., open). Because switches #1, 3, 4 are switched on (i.e., closed), the AC voltage generator 35 will impose a voltage on electrode elements E1, E3, E4. Thermistors T1 and T2 provide a path for current to flow from E1 to E2; thermistors T3 and T2 provide a path for current to flow from E3 to E2; and thermistors T4 and T2 provide a path for current to flow from E4 to E2. This is equivalent to the parallel combination of E1, E3, and E4 wired in series with E2. Because the number of thermistors in this parallel combination increases linearly with the number of electrode elements 52, the current in the single thermistor E2 (which is wired in series with the parallel combination) can become significant. Including the optional additional bank of switches 3L provides the system with the ability to prevent power dissipation in that single thermistor E2 by closing the corresponding switch #2 in bank 3L.

To accomplish this (in those embodiments that include the additional bank of switches 3L), the controller 34 may be programmed so that anytime a given one of the switches in bank 1L is opened, the corresponding switch in bank 3L is closed. This will prevent the thermistor 54 associated with the switched-off electrode element 52 from dissipating too much power, as described in the previous paragraph.

In those embodiments that include the additional bank of switches 3L, individual bypassing of each of the thermistors 54 in the right channel 50R is accomplished using the same approach described above in connection with the left channel 50L, except that the bank of switches 3R is used instead of bank 3L. Corresponding banks of switches (not shown)

are also provided for the other channels 50A, 50P, and a similar approach is used in those channels as well.

Figure 5:
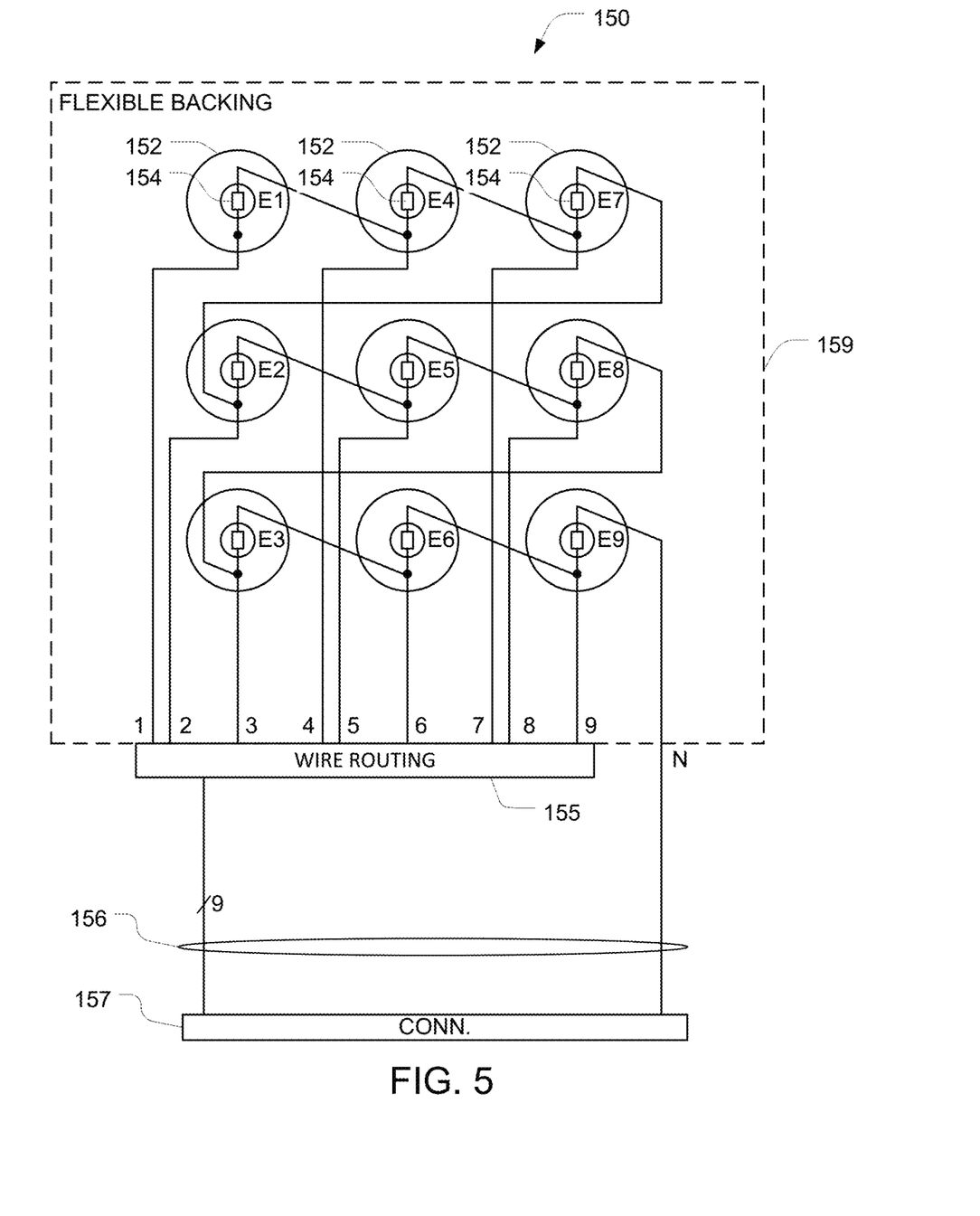
FIG. 5 depicts a second embodiment of a transducer array that provides an individual conductor for each individual electrode element.

FIG. 5 depicts a second embodiment of a transducer array 150 that provides an individual conductor for each individual electrode element 152 without causing a dramatic increase in the number of wires in each cable that runs to a given transducer array, and without requiring active components positioned on or near the transducer arrays. As will be described below in connection with FIG. 6, four copies of the transducer array 150 are preferably used to administer TTFields treatment to a person's head (or other body part).

Each transducer array 150 includes a plurality of electrode elements 152, which are labeled E1-E9 for ease of reference. The electrode elements 152 are similar to the electrode elements 52 described above in connection with the FIG. 3 embodiment. An individual conductor runs from each of the electrode elements 152 to the connector 157 in this FIG. 5 embodiment. These conductors are numbered 1-9 just above the "wire routing" block 155 (which funnels the individual conductors together into a single cable 156). In some preferred embodiments, the electrical connection to each of the electrode elements 152 comprises one or more traces on a flex circuit and/or one or more conductive wires.

In some preferred embodiments, all of the capacitively coupled electrode elements 152 are held in place by a support structure 159, which is similar to the support structure 59 in the FIG. 3 embodiment.

Each transducer array 150 also includes a plurality of thermistors 154, with one thermistor positioned at each of the electrode elements 152 so that the thermistor 154 can sense the temperature of a respective electrode element 152. This may be accomplished as described above in the FIG. 3 embodiment. Each of the thermistors 154 has a first terminal (i.e., the lower terminal of the thermistor in FIG. 5) and a second terminal (i.e., the upper terminal of the thermistor in FIG. 5).

Each transducer array 150 also has a connector 157 that is used to send electrical signals into and out of the transducer array 150. The connector 157 has a plurality of first pins and a second pin. In the illustrated embodiment, the number of first pins is the same as the number of electrode elements 152, and each of the first pins corresponds to a respective one of those electrode elements 152. And in the illustrated embodiment, there is only a single second pin, labeled N. Note that as used herein, the term "pin" can refer to either a male or female pin of the connector 157.

Each transducer array 150 also has a plurality of first conductors, and the number of these first conductors will depend on the number of electrode elements 152. In the embodiment depicted in FIG. 5, which contains 9 electrode elements 152, these conductors are labeled 1-9. Each of these first conductors provides an electrically conductive path between (a) a respective one of the first pins in the connector 157, (b) the conductive substrate of a respective one of the electrode elements 152 (E1-E9), and (c) the first terminal of the corresponding thermistor 154. As in the FIG. 3 embodiment, each of these first conductors may optionally be implemented using a plurality of segments of wire and/or a plurality of traces on a flex circuit.

The plurality of thermistors 154 are arranged in series, beginning with a first one of the thermistors (i.e., the top left in FIG. 5) and ending with a last one of the thermistors (i.e., the bottom right in FIG. 5). The second terminal of each of the thermistors except for the last thermistor is wired to the first terminal of a respective subsequent thermistor.

Each transducer array 150 has a second conductor that provides an electrically conductive path between the second pin of the connector 157 and the second terminal of the last thermistor 154 (i.e., the upper terminal of the bottom right thermistor in FIG. 5). The second conductor may optionally be implemented using a plurality of segments of wire and/or a plurality of traces on a flex circuit.

Because the connector 157 has an individual first pin that corresponds to each of the individual electrode elements 152, and because an electrically conductive path exists between each of the first pins and a respective one of the electrode elements 152, the system that mates with the connector 157 can selectively energize or not energize each of the electrode elements 152 individually by either applying or not applying a signal to the respective first pin on the connector 157. And because the two terminals of any given one of the thermistors 154 are wired to different pins on the connector 157, the system that mates with the connector 157 has access to both terminals of each of the thermistors 154. As a result, the system that mates with the connector 157 can measure the resistance of any of the thermistors 154.

Notably, because any given first pin on the connector 157 corresponds to a respective one of the individual electrode elements 152 and also corresponds to a respective one or two of the individual thermistors 154, each of the first pins on the connector 157 serves two functions. This reduces the number of wires that must be included in each of the cables 156, which in turn advantageously makes the cables more flexible and less cumbersome.

Figure 6:
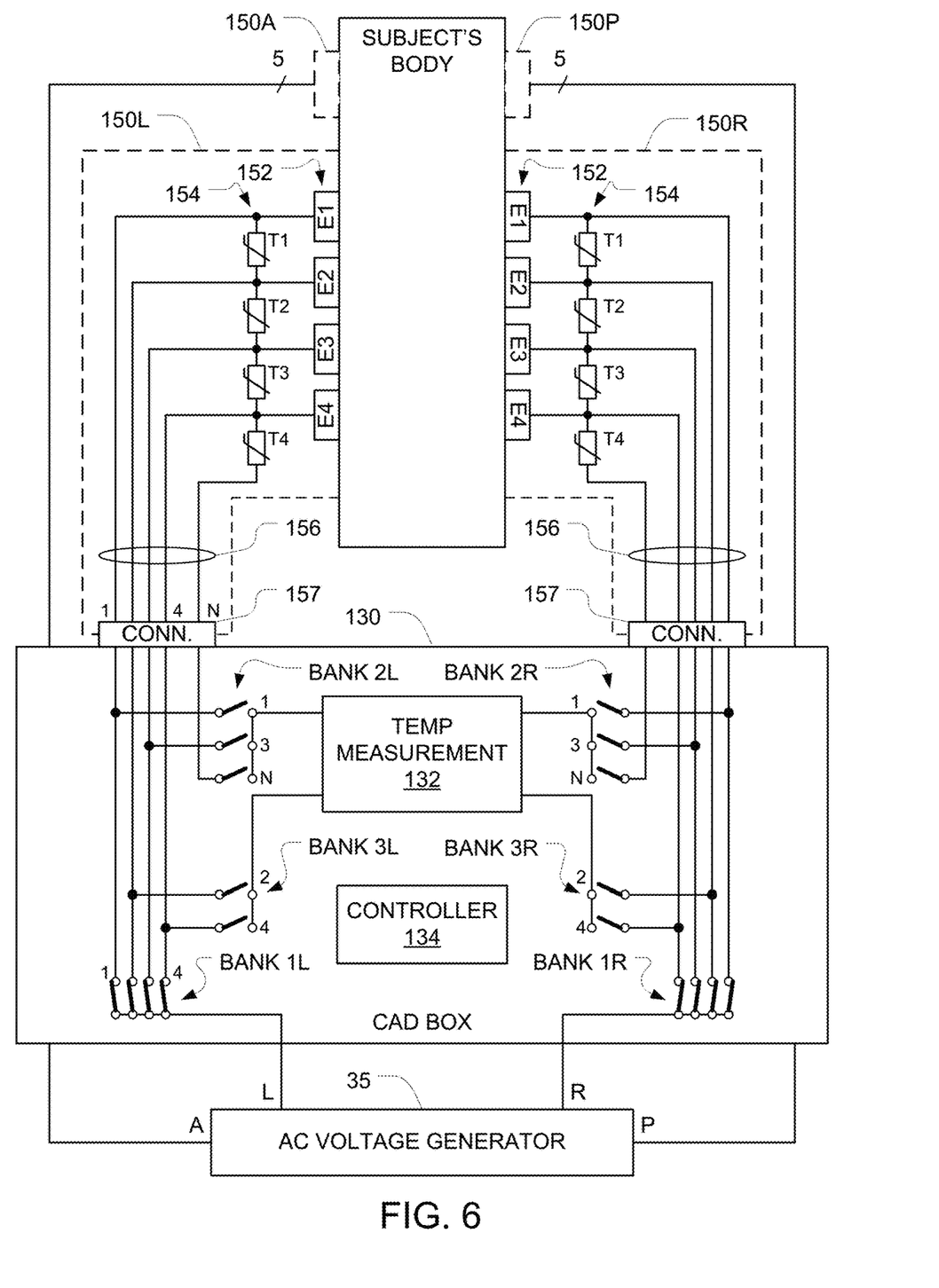
FIG. 6 is a block diagram of a system that uses four copies of the FIG. 5 transducer array to apply TTFields to a subject.

FIG. 6 is a block diagram of a system that uses four copies of the transducer array 150 (described above in connection with FIG. 5) to apply TTFields to a subject. In FIG. 6, these four copies are labeled 150A, 150P, 150L, and 150R, where A, P, L, and R stand for anterior, posterior, left, and right, respectively. The lower portion of FIG. 6 depicts an AC voltage generator 35 and a "CAD box" 130 as separate blocks, the latter of which includes a temperature measurement block 132, a controller 134, and banks of switches 1L, 2L, 3L, 1R, 2R, and 3R. In some embodiments, the components in those two blocks 35, 130 may be physically divided into two separate housings. But in alternative embodiments, the components in those two blocks 35, 130 are combined into a single housing.

For clarity, only the left and right channels are depicted in FIG. 6. But the remaining channels (i.e., the anterior and posterior channels) operate in the same way as the left and right channels, respectively. Additionally, each of the transducer arrays 150 in FIG. 6 is depicted with only 4 electrode elements 152 and four thermistors 154 for purposes of clarity. But it is expected that practical systems will have a larger number (e.g., between 9 and 30) of electrode elements and thermistors, and will also have a larger number of certain other components (e.g., switches, conductors, etc.), depending on the number of electrode elements 152 that are actually used in each of the transducer arrays 150.

The FIG. 6 system can measure the temperatures of the thermistors 154 in the left channel 150L by controlling the electronically-controlled switches in banks 2L and 3L (which may be implemented using bidirectional analog switches) to select each of the thermistors in turn. For example, switches 1 and 2 should be closed to select thermistor T1; switches 2 and 3 should be closed to select thermistor T2; switches 3 and 4 should be closed to select thermistor T3; and switches 4 and N should be closed to select the last thermistor (i.e., T4 in FIG. 6). After any given one of the thermistors T1-T4 within the transducer array 150L has been selected, the temperature measurement block 132 can determine the temperature of that thermistor by measuring the resistance of the thermistor as described above in connection with FIG. 4.

Measuring the temperature of the thermistors 154 in the right channel 150R is accomplished using the same approach described above in connection with the left channel 150L, except that the banks of switches 2R and 3R are used instead of banks 2L and 3L. Corresponding banks of switches (not shown) are also provided for the other channels 150A, 150P, and a similar approach is used in those channels as well.

Based on the temperature readings obtained from the thermistors 154 (T1-T4), the controller 134 controls the switches in banks 1L and 1R (and the corresponding switches in the anterior and posterior channels, not shown) to either turn on or turn off the current (which originates in the AC voltage generator 35) to each of the corresponding electrode elements 152 (E1-E4) as described above in connection with FIG. 4. For example, to leave the current on for all four of the electrode elements 152, all four of the switches in bank 1L should be closed. To interrupt the current that reaches electrode element E1 in channel 150L, switch 1 in bank 1L should be opened; and to interrupt the current that reaches electrode element E2, switch 2 in bank 1L should be opened; etc.

Controlling the current that is routed through individual electrode elements as described above can be used to reduce or eliminate the decrease in average current that is coupled into the person's body when a small number of electrode elements begin to overheat as described above in connection with FIG. 4 (e.g., by reducing the duty cycle to specific electrode elements).

Figure 7:
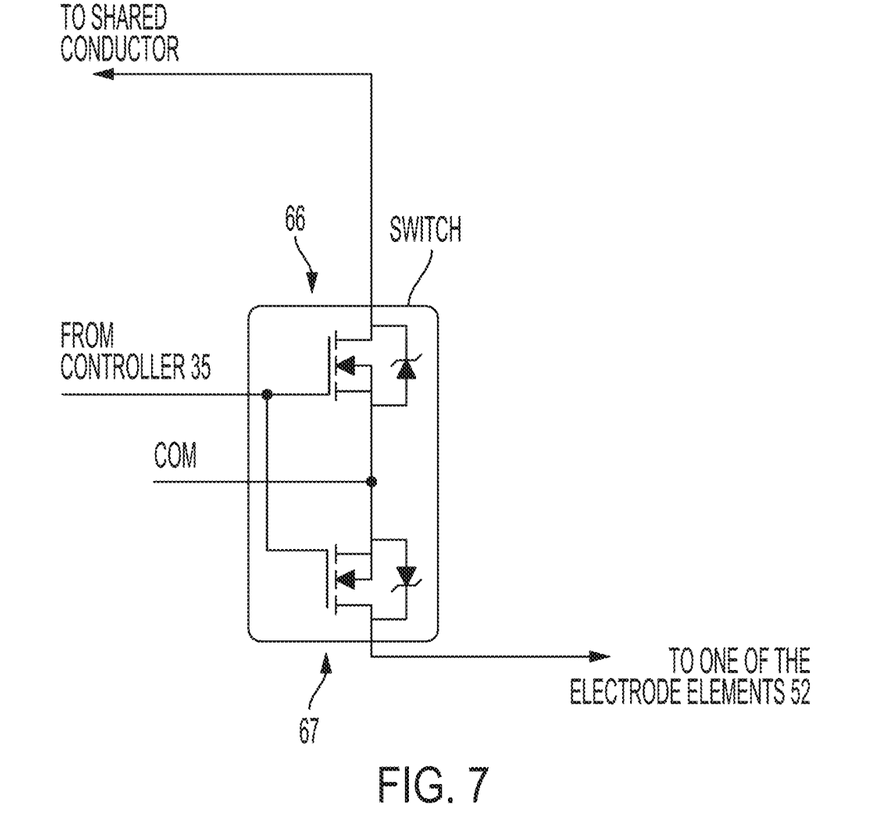
FIG. 7 is a schematic diagram of a circuit that is suitable for implementing each of the switches in banks 1L and 1R in the FIG. 4 and FIG. 6 embodiments.

FIG. 7 is a schematic diagram of a circuit that is suitable for implementing each of the switches in banks 1L and 1R in the FIG. 4 and FIG. 6 embodiments described above, as well as the corresponding banks for the anterior and posterior channels (not shown). The circuit includes two field effect transistors 66, 67 wired in series, which is a configuration that can pass current in either direction. One example of a suitable FET for this circuit is the BSC320N20NSE. (Note that the diodes depicted in FIG. 7 are inherently included within the FETs 66, 67 themselves.) The series combination of the two FETs 66, 67 will either conduct or block the flow of electricity, depending on the state of the control input that arrives from one of the digital outputs of the controller 34 described above. When the series combination is conducting, current can flow between the shared conductor and the respective electrode element 52. On the other hand, when the series combination of FETs 66, 67 is not conducting, current will not flow between the shared conductor and the respective electrode element 52.

In the embodiments described above in connection with FIGS. 3 and 5, all of the electrode elements 52 are capacitively coupled, and the support structure 59 is configured to hold the electrode elements 52 against the subject's body so that the dielectric layer of the electrode elements 52 faces the subject's body and can be positioned in contact with the subject's body. But in alternative embodiments, the electrode elements that are not capacitively coupled may be used. In this case, the dielectric layer of each electrode element is omitted, in which case the support structure 59 holds the electrode elements 52 against the subject's body so a conductive surface of the electrode elements 52 faces the subject's body and can be positioned in contact with the subject's body. Optionally, in these embodiments, a layer of hydrogel may be disposed between the conductive surface of the electrode elements 52 and the subject's body when the transducer array 50 is placed against the subject's body.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus for applying an alternating electric field to a subject's body, the apparatus comprising:
   a plurality of electrode elements;
   a support configured to hold the electrode elements against the subject's body;
   a plurality of thermistors, each of the thermistors having a first terminal and a second terminal, wherein each of the thermistors is positioned to sense a temperature at a corresponding respective one of the electrode elements;
   a connector having a plurality of first pins and a second pin;
   a plurality of first conductors, each of which provides an electrically conductive path between (a) a respective one of the first pins, (b) a respective one of the electrode elements, and (c) the first terminal of the corresponding thermistor; and
   a second conductor that provides an electrically conductive path between the second pin and the second terminal of at least one of the thermistors.

2. The apparatus of claim 1, wherein the second terminals of all the thermistors are wired together.

3. The apparatus of claim 2, wherein the second terminals of all the thermistors are wired together using at least one of (a) at least one trace on a flex circuit and (b) at least one wire.

4. The apparatus of claim 1, wherein the plurality of thermistors are arranged in series, beginning with a first one of the thermistors and ending with a last one of the thermistors, and wherein the second terminal of each of the thermistors except for the last thermistor is wired to the first terminal of a respective subsequent thermistor, and wherein the second conductor provides an electrically conductive path between the second pin of the connector and the second terminal of the last thermistor.

5. The apparatus of claim 1, wherein the second conductor provides an electrically conductive path between the second pin and the second terminal of only a single one of the thermistors.

6. The apparatus of claim 1, wherein the plurality of electrode elements comprises at least four electrode elements, and wherein the plurality of thermistors comprises at least four thermistors.

7. The apparatus of claim 1, wherein the plurality of electrode elements comprises at least nine electrode elements, and wherein the plurality of thermistors comprises at least nine thermistors.

8. The apparatus of claim 1, wherein each of the electrode elements comprises a conductive plate and a dielectric layer disposed on the conductive plate, and wherein the support is configured to hold the electrode elements against the subject's body so that the dielectric layer of each of the electrode elements faces the subject's body.

9. The apparatus of claim 1, wherein the second terminals of all the thermistors are wired together, and wherein the second conductor provides an electrically conductive path between the second pin and the second terminal of all the thermistors.

\* \* \* \* \*